United States Patent [19]
Daly et al.

[11] Patent Number: 6,114,585
[45] Date of Patent: Sep. 5, 2000

[54] ETHER AMINES FROM 2-PENTENENITRILE

[75] Inventors: Thomas J. Daly, Barrington, Ill.; Anita Mokadam Sorhaug; Robert E. Harbour, Jr., both of Houston, Tex.; Abraham A. Zahand, Kingswood, Tex.; Michael Clumpner, Delavan, Wis.; Anthony J. O'Lenick, Jr., Dacula, Ga.

[73] Assignee: Nova Molecular Technologies Inc, Janesville, Wis.

[21] Appl. No.: 09/459,562

[22] Filed: Dec. 13, 1999

[51] Int. Cl.[7] .......................... C07C 217/28; C07C 217/42
[52] U.S. Cl. ............................ 564/505; 564/503; 564/504
[58] Field of Search ...................................... 564/503, 504, 564/505

[56] References Cited

U.S. PATENT DOCUMENTS 5,070,202  12/1991  Herkes .
5,540,337   7/1996  Riggs et al. ............................. 209/166

*Primary Examiner*—Samuel Barts
*Assistant Examiner*—Brian J. Davis

[57] ABSTRACT

The present invention relates to a series of novel ether amine compounds prepared by the cyanobutylation reaction of an alcohol having 12 to 26 carbon atoms with 2-pentenenitrile to form a branched alkyl ether nitrile. The etheraminonitriles formed by the process are hydrogenated to form alkylether amines. The resulting product can be reacted with 2-pentenenitrile and hydrogenated to yield a polyamine.

24 Claims, No Drawings

ETHER AMINES FROM 2-PENTENENITRILE

FIELD OF THE INVENTION

The present invention relates to a series of novel ether amine compounds prepared by the cyanobutylation reaction of an alcohol having 12 to 26 carbon atoms with 2-pentenenitrile to form a branched alkyl ether nitrile. The ether nitrites formed by the process are hydrogenated to form alkylether amines. The resulting product can be reacted with 2-pentenenitrile and hydrogenated to yield a polyamine.

BACKGROUND OF THE INVENTION

U.S. Pat. Nos. 4,260,556 and 4,211,725 teach reaction of 2-pentenenitrile with ammonia or ethylenediamine to produce alkylaminonitriles. U.S. Pat. No. 4,496,474 teaches the reaction of 2-pentenenitrile with alkylamines having from 8 to 22 carbons to produce the corresponding nitrile compound. U.S. Pat. No. 5,070,202 teaches a process having improved reaction rate and selectivity in the reaction of 2-pentenenitrile with amines to form alkylaminonitriles by the incorporation of from 15 to 60 weight percent water in the reaction mixture. These references do not include the critical ether linkage needed to make the products of the present invention.

U.S. Pat. No. 5,902,883 to Herkes discloses the cyanobutylation of various amines to make diamines. Herkes uses 3-pentenenitrile, 4-pentenenitrile or mixtures of 3-pentenenitrile and 4-pentenenitrile to make his product. This does not result in the desired branching that comes from the compounds of the present invention, nor does it include the critical ether linkage in the molecule. Herkes has done some work with the cyanobutylation of lower molecular weight alcohols (C3 to C8). These materials lack the hydrophobicity to produce good surface-active agents.

It has now been found that by reacting alcohols with 2-pentenenitrile, products with unique properties result. These include (a) higher purity (i.e. less homopolymerization of the nitrile); (b) superior liquidity of the resulting products, (c) improved surfactant properties and (d) improved solubility in hydrocarbons. All of these will become clear as one reads the teachings of the present invention.

SUMMARY OF THE INVENTION

The present invention discloses novel ether amine compounds. These are made by the reaction sequence comprising the steps of reacting an alcohol having 12 to 26 carbon atoms with 2-pentenenitrile, then hydrogenating the resulting nitrile to an ether amine. Optionally, the entire process can be repeated with the ether amine to give diamines and polyamines. The selection of the alkyl groups having between 12 and 26 carbon atoms is very important in that compounds having this number of carbon atoms in the hydrophobe are surface active agents. Compounds of this class having less carbon atoms in the molecule do not possess foaming or emulsification properties. Compounds having more carbon atoms in the molecule are too insoluble in water to be effective surfactants.

The resulting ether amines conform to the following structure:

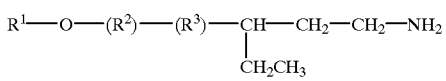

$R^1$ is selected from the group consisting of alkyl having 12 to 26 carbon atoms,
$R^2$ is $—(CH_2CH_2O)_3—(CH_2CH(CH_3)O)_b—(CH_2CH(CH_2CH_3)O)_c—$
a, b and c are independently integers ranging from 0 to 20,
$R^3$ is

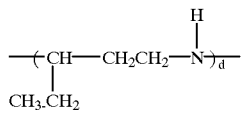

d is 0 or 1.

The introduction of the ether group, along with the branched ethyl group ($—CH_2CH_3$) results not only in products that surprisingly improved properties over the linear and non-ether products, but also offers a number of property and process improvements that are not possible using acrylonitrile based technologies. 2-pentenenitrile made by The DuPont Company may contain a portion of an isomer 2-methyl-2-butenenitrile. This other isomer of the 2-pentenenitrile may be present in the reaction process. It will react giving a different branched product. We prefer to use 2-pentenenitrile in our processes, but the commercial grade available from The DuPonte Company that has up to 30% 2-methyl-2-butenenitrile present with the 2-pentenenitrile may also be used.

The products of the present invention offer several unexpected improvements over acrylonitrile chemistries. Firstly, the purity of the product is improved. This is because the competitive reaction, namely homopolymerization, is minimized. In producing alkoxypropyl amines from acrylonitrile, a major difficulty is encountered in the hydrogenation reaction. This problem was traced to the homopolymerization of acrylonitrile when forming the alkoxypropionitrile. The homopolymer of acrylonitrile poisons the hydrogenation catalyst and inactivates it. In order to cope with this very undesirable by-product, chemical manufacturers have developed an extraction procedure utilizing a water wash to remove the homopolymer from the nitrile. This results not only in loss of product but a disposal problem. We have surprisingly learned that by using 2-pentenenitrile we substantially minimize the problem of homopolymerization, especially with high molecular weight, high melting point and branched hindered molecules. This is attributed to the chemistry of this material and its reduced tendency to homopolymerize.

The selection of the alcohol for cyanobutylation results in the favorable condition that $k^2 >> k^1$

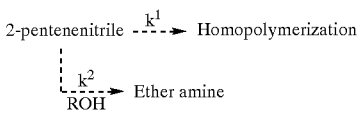

Consequently, very little homopolymer is encountered and the purity of product is improved. When one compares this situation to the acrylonitrile based reactions wherein;

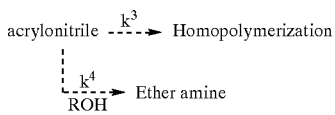

$k^3$ is much closer in magnitude to $k^4$. On a practical level this means that the homopolymerization reaction will be much more competitive with the desired reaction and a lot of homopolymer will form.

Another area in which the compounds of the present invention offer improvements over acrylonitrile chemistries relates to high melting raw materials, or raw materials having secondary hydroxyl groups. The reaction of any nitrile with any alcohol needs to be a liquid in liquid reaction. Consequently, in the case where the alcohol has a high melting point, the reaction temperature must be high. This results in a very large concentration of homopolymer when acrylonitrile is used, but little or no homopolymer when 2-pentenenitrile is used. In instances where the hydroxyl group being reacted is secondary, as in the case of polyoxypropylene containing molecules, the reaction with 2-pentenenitrile can be conducted with a larger excess and at higher temperatures than could be used with acrylonitrile products. This is related to the lower rate of homopolymerization encountered using 2-pentenenitrile. In addition, the boiling point of the 2-pentenenitrile is much greater than that of the acrylonitrile, which coupled with 2-pentenenitrile's lower tendency to homopolymerize allows for reaction at higher temperature while at low pressure.

Another advantage of using 2-pentenenitrile in the preparation of amines is likewise related to the slow homopolymerization. We have learned that since hompolymerization is minimized using 2-pentenenitrile when compared to acrylonitrile, an excess of 2-pentenenitrile can be used in the reaction and the excess simply stripped off. This allows for more complete reactions and less by-product concentration. Additionally, the resulting ether nitrile may also be distilled under vacuum without concern that the nitrile will break down into its constituents.

The introduction of the ether group into the molecule together with the specific ethyl branching introduced by using 2-pentenenitrile results in a product having superior liquidity. Liquidity is a property desirable in many applications. There are not many options available to improve liquidity. The material with the highest melting point in a series is the fully saturated product. One way to improve liquidity is to introduce unsaturation. This is why oleyl products with one double bond are much more liquid than stearyl products that have the same number of carbon atoms but no double bonds. The difficulty here is that double bonds are susceptible to a process known as rancidity. This process breaks the double bond and forms aldehydic components that are not only reactive with each other, but also have mal odor and mal taste. This instability limits the utility of unsaturated materials in many applications. We have found that improved liquidity is achieved by introduction of the ether group and the branching found in the 2-pentenenitrile. Standard ether amines that are made with acrylonitrile result in linear materials that do not have the same degree of improved liquidity as the ether amines that are derived from using 2-pentenenitrile in place of acrylonitrile. The introduction of the branching allows for improved solvency, and ease of formulation and use.

DETAILED DESCRIPTION

The present invention relates to novel ether amines prepared by the cyanobutylation reaction of an alcohol having 12 to 26 carbon atoms with 2-pentenenitrile to form branched alkyl ether nitrile. The ether nitrites formed by the process are hydrogenated to form alkylether amines. The resulting ether amine can be further reacted with 2-pentenenitrile, then hydrogenated to yield a diamine. These two processes can then be repeated to form polyamines. The selection of the alkyl group value from 12 to 26 is very important. It is over this relatively narrow range that the optimum emulsification and corrosion inhibition properties are encountered.

The technology provides a series of ethyl branched ether amine compounds that conform to the

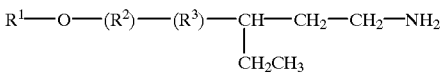

$R^1$ is selected from the group consisting of akyl having 12 to 26 carbon atoms,
$R^2$ is $—(CH_2CH_2O)_a—(CH_2CH(CH_3)O)_b—(CH_2CH(CH_2CH_3)O)_c—$;
a b and c are independently integers ranging from 0 to 20, $R^3$ is

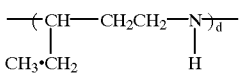

d is 0 or 1.

The most commonly used alcohols are linear products that have no branching in them. In a preferred embodiment the alcohols are branched. In one such instance they have methyl branching in them. They are typically derived from the oxo alcohol process. Oxo alcohols are prepared by the reaction of alpha olefin with hydrogen and carbon monoxide using a catalyst, commonly cobalt. The reaction occurs in two parts, the first is the preparation of the aldehyde and the second is reduction of the aldehyde to the alcohol. The branching pattern on the alcohols utilized in the practice of the present invention can be quite varied without effecting the ability to make the products of the present invention.

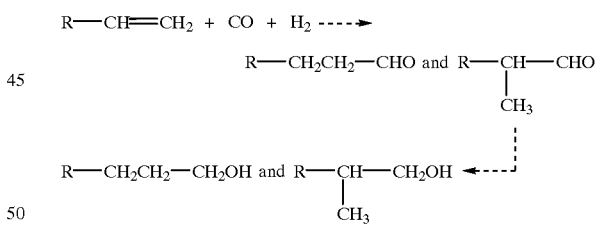

In another preferred embodiment, the alcohol is a guerbet alcohol. Guerbet Alcohols are known in the art and are regiospecifically beta branched alcohols. They have been known since the 1890's when Marcel Guerbet first synthesized them. (M. Guerbet, C. R. Acad. Sci. Paris, 128, 511; 1002 (1899)). These materials are high in molecular weight and are liquid to very low temperatures. The guerbet reaction gives very specific branching in the alcohol as shown;

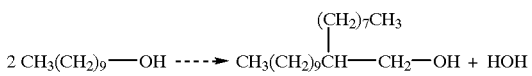

As can be seen by the above reaction the molecules have substitution on the second carbon from the hydroxyl group.

There are two classes of compounds and several sub classes of compounds embodied within the generic structure.

Class 1: Ether monoamine (d=0)
The ether monoamines conform to the following structure:

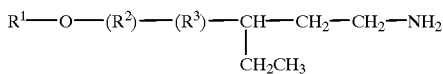

wherein;
$R^1$ is selected from the group consisting of alkyl having 12 to 26 carbon atoms
$R^2$ is $-(CH_2CH_2O)_a-(CH_2CH(CH_3)O)_b-(CH_2CH(CH_2CH_3)O)_c-$;
a, b and c are independently integers ranging from 0 to 20,
$R^3$ is

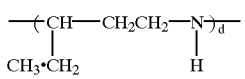

d is 0.

Preferred Embodiments for Ether Monoamines

In a preferred embodiment for ether monoamines, d is 0 and $R^1$ is $C_{12}H_{25}$, a, b and c are each 0.

In a preferred embodiment for ether monoamines, d is 0 and $R^1$ is $C_{13}H_{27}$, a, b and c are each 0.

In a preferred embodiment for ether monoamines, d is 0 and $R^1$ is guerbet $C_{16}H_{33}$, a, b and c are each 0.

In a preferred embodiment for ether monoamines, d is 0 and $R^1$ is $C_{18}H_{37}$, a, b and c are each 0.

In a preferred embodiment for ether monoamines, d is 0 and $R^1$ is guerbet $C_{26}H_{53}$, a, b and c are each 0.

In a preferred embodiment for ether monoamines, d is 0 and $R^1$ is $C_{13}H_{27}$, a is 5 and b and c are each 0.

In a preferred embodiment for ether monoamines, d is 0 and $R^1$ is $C_{12}H_{25}$, a is 20 and b and c are each 0.

In a preferred embodiment for ether monoamines, d is 0 and $R^1$ is guerbet $CH_{16}H_{33}$, a is 0, b is 20 and c is 0.

In a preferred embodiment for ether monoamines, d is 0 and $R^1$ is $C_{13}H_{27}$, a and b are 0 and c is 20.

In a preferred embodiment for ether monoamines, d is 0 and $R^1$ is $C_{13}H_{27}$, a and b are 10 and c is 0.

Class 2: Ether diamine (d=1)
Ether diamine compounds of the present invention conform to the following structure:

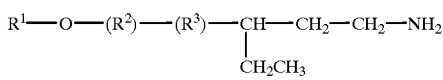

$R^1$ is selected from the group consisting of alkyl having 12 to 26 carbon atoms
$-(CH_2CH_2O)_a-(CH_2CH(CH_3)O)_b-(CH_2CH(CH_2CH_3)O)_c-$;
a, b and c are independently integers ranging from 0 to 20,
$R^3$ is

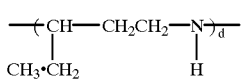

d is 1.

Preferred Embodiment

In a preferred embodiment for ether diamines, d is 1 and $R^1$ is $C_{12}H_{25}$, a, b and c are each 0.

In a preferred embodiment for ether diamines, d is 1 and $R^1$ is $C_{13}H_{27}$, a, b and c are each 0.

In a preferred embodiment for ether diamines, d is 1 and $R^1$ is guerbet $C_{16}H_{33}$, a, b and c are each 0.

In a preferred embodiment for ether diamines, d is 1 and $R^1$ is $C_{18}H_{37}$, a, b and C are each 0.

In a preferred embodiment for ether diamines, d is 1 and $R^1$ is guerbet $C_{26}H_{53}$, a, b and C are each 0.

In a preferred embodiment for ether diamines, d is 1 and $R^1$ is $C_{13}H_{27}$, a is 5 and b and c are each 0.

In a preferred embodiment for ether diamines, d is 1 and $R^1$ is $C_{12}H_{25}$, a is 20 and b and c are each 0.

In a preferred embodiment for ether diamines, d is 1 and $R^1$ is guerbet $C_{16}H_{33}$, a is 0, b is 20 and c is 0.

In a preferred embodiment for ether diamines, d is 1 and $R^1$ is $C_{13}H_{27}$, a and b are 0 and c is 20.

Preferred embodiment for ether diamines, d is 1 and $R^1$ is $C_{13}H_{27}$, a and b are 10 and c is 0.

Raw Materials

Alcohols

The alcohols and alcohol alkoxylates used in the manufacture of the products of the present invention are well known in the art and are commercially available from a variety of suppliers. Suppliers of these materials include Shell Chemical Company, Condea-Vista and Exxon Chemical Company in Houston, Tex. and Siltech Corporation in Toronto Canada.

$R^1-O-(CH_2CH_2O)_a-(CH_2CH(CH_3)O)_b-(CH_2CH(CH_2CH_3)O)_c-H$

|  |  | $R^2$ |  |  |
|---|---|---|---|---|
| Example | $R^1$ | a | b | c |
| 1 | $C_{12}H_{25}$ | 0 | 0 | 0 |
| 2 | $C_{13}H_{27}$ | 0 | 0 | 0 |
| 3 | guerbet $C_{16}H_{33}$ | 0 | 0 | 0 |
| 4 | $C_{18}H_{37}$ | 0 | 0 | 0 |
| 5 | guerbet $C_{26}H_{55}$ | 0 | 0 | 0 |
| 6 | $C_{13}H_{27}$ | 5 | 0 | 0 |
| 7 | $C_{12}H_{25}$ | 20 | 0 | 0 |
| 8 | guerbet $C_{16}H_{33}$ | 0 | 20 | 0 |
| 9 | $C_{13}H_{27}$ | 0 | 0 | 20 |
| 10 | $C_{13}H_{27}$ | 10 | 10 | 0 |

Procedure

Preparation of Ether Nitrile (Cyanobutylation)

One mole of base alcohol is charged to a reaction flask and one mole plus approximately 10% excess of the 2-pentenenitrile is placed in an addition flask. Material is heated while stirred to a temperature of about 40° C. Base catalyst (KOH) is added based on the total weight of the reactants charged at about a 0.1 to 0.5% or more preferably 0.2–0.3% basis. A nitrogen blanket is applied to the headspace of the reaction vessel and the mixture is stirred for about 15 minutes at 40° C. to incorporate the catalyst into the alcohol. Keep the reaction flask headspace blanketed with nitrogen throughout the entire reaction period.

The addition of the 2-pentenenitrile is exothermic. Charge the 2-pentenentrile to the reaction vessel such that the temperature of reaction is maintained at 40–65° C., more preferably 45–60° C., and most preferably 50–55° C. When all of the 2-pentenenitrile has been added let react for 2 hours at 50° C. After the 2 hours add an equivalent amount of acid to neutralize the base catalyst. Stir mixture for 15 minutes then filter the 3-alkoxy-3-ethylpropylnitrile to be hydrogenated to remove salts formed on neutralization of the KOH.

Hydrogenation of 3-alkoxypentanenitrile

Charge the ether nitrile to an autoclave that is capable of operating at pressures up to 600 psig. Charge 2% by weight of Raney Nickel (based upon the weight of the alcohol to the vessel). Seal autoclave and start agitation, increase heat to about 80 to 100° C. and vacuum strip out any water that may have been introduced during cyanobutylation or from Raney nickel. When no more water appears on the condenser of the vacuum set-up, close autoclave and charge hydrogen gas to about 5 psig. Charge ammonia to vessel to about 60 to 70 psig. Increase heat to 135° C. and note pressure. Add hydrogen such that about 150 to 200 psig additional pressure is measured on the autoclave pressure gauge. Maintain continuous hydrogen addition in this manner for a period of 4–6 hours, then close the hydrogen inlet valve and note pressure on the pressure gauge.

Turn off heat and cool to about 70° C. Carefully, open vent to release pressure and vacuum strip to remove ammonia. Discharge the 3-alkoxy-3ethylpropylamine and filter to remove Raney nickel catalyst.

EXAMPLE 11

(Preparation of 3-dodecoxy-3-ethylpropylnitrile) (Cyanobutylation)

To a 500 ml round bottomed flask fitted with a mechanical stirrer, gas inlet tube and dropping funnel was added 185 g (1 mole) of n-dodecyl alcohol (Example 1) and 0.7 g of KOH. A nitrogen blanket was maintained throughout the procedure. The temperature was increased to 40° C. while stirring to dissolve and disperse the KOH. The dropping funnel was charged with 90.0 g of 2-pentenenitrile (1.11 mole). The nitrile was added with stirring at a rate that kept the reaction temperature from rising over 50° C. After the addition the reaction was allowed to proceed for an additional 2 hours and 50° C. The catalyst, KOH, was then deactivated by neutralization with an equivalent amount of acetic acid. After neutralization the mixture was stirred for 15 minutes and then filtered to remove the salts that formed on neutralization. The excess 2-pentenenitrile was then removed by vacuum stripping Preparation of dodecyloxypentylamine— (Hydrogenation)

The 265 g (0.99 mole) of 3-dodecyloxy-3-ethylpropylnitrile was poured into a 500 ml stirred Autoclave Engineers autoclave. Raney® nickel, 5.3 g was also added. After sealing the autoclave and heating to 80° C. a vacuum was applied while stirring to remove water introduced with the catalyst. When no more water appeared on the condenser of the vacuum set-up the vacuum was released and hydrogen was allowed to fill the vessel to a pressure of 5 psig. Ammonia was then added until the pressure rose to 65 psig. The temperature was then increased to 135° C. that caused the pressure to rise to about 150 psig.. The pressure was then increased to 400 psig with hydrogen and the stirring speed increased to 1200 rpm. After 4 hours the valve to the hydrogen cylinder was closed and the pressure in the head space monitored. Since the pressure dropped by 100 psig over the next 15 minutes, the valve was opened again and the reaction allowed to proceed for another hour. After checking for a pressure drop again, none was noted over the next 15 minutes and the reaction was declared complete. The heat was turned off and cooling water run through the coils until the temperature dropped to 70° C. After venting off the hydrogen and flushing with nitrogen, residual ammonia was vacuum stripped. The product, 3-n-dodecoxy-3-ethylpropylamine, was filtered to remove Raney® nickel catalyst. The yield was essentially quantitative.

EXAMPLE 12–20

Example 11 is repeated, only this time replacing the alcohol example with the type and quantity of alcohol shown.

|  | Alcohol | | KOH (95%) |
|---|---|---|---|
| Example | Example | Grams | Grams |
| 12 | 2 | 200.0 | 0.7 |
| 13 | 3 | 206.0 | 0.8 |
| 14 | 4 | 270.0 | 0.9 |
| 15 | 5 | 385.0 | 1.2 |
| 16 | 6 | 421.0 | 1.3 |
| 17 | 7 | 1,070.0 | 2.7 |
| 18 | 8 | 1,404.0 | 3.8 |
| 19 | 9 | 1,642.0 | 4.4 |
| 20 | 10 | 1,222.0 | 3.3 |

The products are used as prepared, or may be used in aqueous systems by neutralizing them with a stoichiometric amount of an acid like HCl, $H_2SO_4$, or acetic acid.

Class 2: Etherdiamine (d is 1)
Procedure

The products of class 1 are reacted with additional 2-pentenenitrile to make the ether aminonitrile, then subsequently reacted with hydrogen to make the ether diamine. Unlike the cyanobutylation of the alcohol, no base catalyst is added to the cyanobutylation process for the ether amine.

EXAMPLE 21

Preparation of 3-(3'-dodecoxy-3'-ethylpropylamino) pentanenitrile (Cyanobutylation)

To a suitable reaction flask is added 275.0 grams of 3-dodecoxypentylamine (example 11). Heat while under agitation to 40° C. Apply a nitrogen blanket is applied to the headspace of the reaction vessel and the mixture is stirred for about 15 minutes at 40° C. to incorporate the catalyst into the alcohol. Keep the reaction flask headspace blanketed with nitrogen throughout the entire reaction period. Begin addition of 90.0 grams of 2-pentenenitrile under good agitation keeping the temperature below 50° C. When all of the 2-pentenenitrile has been added let react for 2 hours at 50° C.

Preparation of Etheramine (Hydrogenation)

Charge the etheramine pentanitrile as prepared to an autoclave that is capable of operating at pressures up to 600 psig. Autoclave must be placed in a hood or vented area and must be equipped with vacuum stripping, cooling, and heating. Carefully charge a known quantity of metal catalyst such as Raney Nickel to the vessel. Use 2% by weight based upon the weight of the total batch. Seal autoclave and start agitation, increase heat to about 80 to 100° C. and vacuum strip out any water that may have been introduced during cyanobutylation or from Raney nickel. When no more water, appears on the condenser of the vacuum set-up, close autoclave and charge hydrogen gas to about 5 psig. Charge ammonia to vessel up to about 60 to 70 psig. Increase heat to 135° C. and note pressure. Add Hydrogen such that about 150 to 200 psig additional pressure is measured on the autoclave pressure gauge. Maintain this increase with hydrogen gas that will be rapidly taken up by the reaction mixture during the first hour of the reaction. Maintain continuous hydrogen addition in this manner for a period of 4 to 6 hours, After this time, close the valve from the hydrogen to the autoclave and note pressure on pressure gauge. If pressure is stable and does not decrease after 15 minutes, reaction is complete, otherwise continue adding hydrogen as described previously for one hour and then re-check.

Example 21 is repeated, only this time replacing the ether monoamine of example 12 with the type and quantity of monoether amine shown.

| | Ether monoamine | |
|---|---|---|
| Example | Example | Grams |
| 22 | 12 | 285.0 |
| 23 | 13 | 292.0 |
| 24 | 14 | 356.0 |
| 25 | 15 | 470.0 |
| 26 | 16 | 506.0 |
| 27 | 17 | 1,156.0 |
| 28 | 18 | 1,489.0 |
| 29 | 19 | 1,728.0 |
| 30 | 20 | 1,307.0 |

The products are prepared, or may be used in aqueous systems by neutralizing them with a stoichiometric amount of an acid like HCl, $H_2SO_4$, or acetic acid.

The compounds of the present invention are liquid products useful as surface active agents and as raw materials for derivatives. In order to demonstrate the properties of the amines of the present invention materials having about the same molecular weight were prepared and evaluated. These included:

(1) dodecyloxypentylamine (example 11),—(a compound of the present invention)
(2) Hydrogenated tallow amine $C_{18}H_{37}NH_2$ (a linear alkyl amine marketed as Armeen HT from Akzo Nobel Chemicals, Chicago Ill.)

and
Tetradecyloxypropylamine $C_{14}H_{29}$—O—$(CH_2)_3NH_2$ (an ether amine based upon acrylonitrile chemistry marketed by Tomah Products Inc. Milton Wis. As PA-18)

| | Hydrogenated Tallow Amine | Tetradecyloxy-proplyamine | Example 11 |
|---|---|---|---|
| Total Amine Value | 207 | 190 | 197 |
| Molecular Weight | 271 | 280 | 285 |
| Pour Point ° C. | 42 | 20 | −24 |
| Miscibility in Heptane | immiscible | turbid | miscible |
| Miscibility in Kerosene | immiscible | miscible | miscible |

The data above shows that although the compound of the present invention (Example 11) has the highest molecular weight of the products tested, it has a significantly lower pour point. It is 44° C. lower than the acrylonitrile based chemistry and 66° C. lower than the linear product. The product of the present invention is not only liquid at lower temperatures, but also has improved miscibility in heptane and kerosene.

Pour point was determined using ASTM method D97 and miscibility in heptane and kerosene were determined using ASTM D1467

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. An ether amine conforming to the following structure:

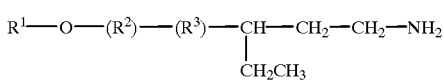

$R^1$ is selected from the group consisting of alkyl having 12 to 26 carbon atoms,
$R^2$ is —$(CH_2CH_2O)_a$—$(CH_2CH(CH_3)O)_b$—$(CH_2CH(CH_2CH_3)O)_c$—
a b and c are independently integers ranging from 0 to 20, with the proviso that a, b and c are not all zero;
$R^3$ is

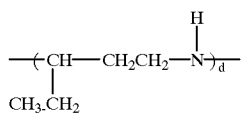

d is 0 or 1.

2. An ether amine of claim 1 wherein d is 0.
3. An ether amine of claim 2 wherein $R^1$ is $C_{12}H_{25}$.
4. An ether amine of claim 2 wherein $R^1$ is $C_{13}H_{27}$.
5. An ether amine of claim 2 wherein $R^1$ is guerbet $C_{16}H_{33}$.
6. An ether amine of claim 2 wherein $R^1$ is $C_{18}H_{35}$.
7. An ether amine of claim 2 wherein $R^1$ is guerbet $C_{26}H_{53}$.
8. An ether amine of claim 2 wherein $R^1$ is $C_{13}H_{26}$, a is 5 and b and c are 0.
9. An ether amine of claim 2 wherein $R^1$ is $C_{12}H_{25}$, a is 20, b is 0 and c is 0.
10. An ether amine of claim 2 wherein $R^1$ is guerbet $C_{16}H_{33}$, a is 0, b is 20 and c is 0.
11. An ether amine of claim 2 wherein $R^1$ is $C_{13}H_{26}$, a is 0, b is 0, and c is 20.
12. An ether amine of claim 2 wherein $R^1$ is $C_{13}H_{26}$, a is 10, b is 10, and c is 0.

13. An ether amine conforming to the following structure:

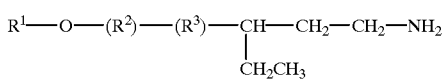

$R^1$ is selected from the group consisting of alkyl having 12 to 26 carbon atoms,
$R^2$ is $-(CH_2CH_2O)_a-(CH_2CH(CH_3)O)_b-(CH_2CH(CH_2CH_3)O)_c-$
a b and c are independently integers ranging from 0 to 20,
$R^3$ is

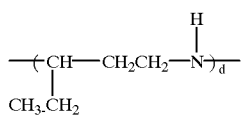

d is 1.

14. An ether amine of claim 13 wherein a, b and c are each 0.

15. An ether amine of claim 13 wherein $R^1$ is $C_{12}H_{25}$.

16. An ether amine of claim 13 wherein $R^1$ is $C_{13}H_{27}$.

17. An ether amine of claim 13 wherein $R^1$ is guerbet $C_{16}H_{33}$.

18. An ether amine of claim 13 wherein $R^1$ is $C_{18}H_{35}$.

19. An ether amine of claim 13 wherein $R^1$ is guerbet $C_{26}H_{53}$.

20. An ether amine of claim 13 wherein $R^1$ is $C_{13}H_{26}$, a is 5 and b and c are 0.

21. An ether amine of claim 13 wherein $R^1$ is $C_{12}H_{25}$, a is 20, b is 0 and c is 0.

22. An ether amine of claim 13 wherein $R^1$ is guerbet $C_{16}H_{33}$, a is 0, b is 20 and c is 0.

23. An ether amine of claim 13 wherein $R^1$ is $C_{13}H_{26}$, a is 0, b is 0, and c is 20.

24. An ether amine of claim 13 wherein $R^1$ is $C_{13}H_{26}$, a is 10, b is 10, and c is 0.

* * * * *